United States Patent
Ryu et al.

(10) Patent No.: US 8,486,404 B2
(45) Date of Patent: Jul. 16, 2013

(54) ANTIBODY SPECIFICALLY BINDING TO ANGIOPOIETIN-2 AND USE THEREOF

(75) Inventors: Jong-sang Ryu, Suwon-si (KR); Brian Ho-sung Min, Seongnam-si (KR); A-yeon Cho, Seongnam-si (KR); Min-kyung Kim, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 287 days.

(21) Appl. No.: 12/968,500

(22) Filed: Dec. 15, 2010

(65) Prior Publication Data

US 2011/0150895 A1  Jun. 23, 2011

(30) Foreign Application Priority Data

Dec. 15, 2009  (KR) .................. 10-2009-0125035

(51) Int. Cl.
| | |
|---|---|
| *C07K 16/22* | (2006.01) |
| *A61K 39/395* | (2006.01) |
| *C12N 5/12* | (2006.01) |
| *A61P 35/04* | (2006.01) |
| *C12N 15/13* | (2006.01) |
| *C12N 15/85* | (2006.01) |
| *G01N 33/566* | (2006.01) |

(52) U.S. Cl.
USPC .................................. 424/145.1; 530/388.23

(58) Field of Classification Search
CPC ... C07K 16/22; C07K 2317/24; C07K 2317/76
USPC .................................. 424/145.1; 530/388.23
See application file for complete search history.

(56) References Cited

U.S. PATENT DOCUMENTS 7,534,604 B2  5/2009 Fandl et al.

FOREIGN PATENT DOCUMENTS

| WO | 03/030833 A3 | 4/2003 |
|---|---|---|
| WO | 2006/068953 A2 | 6/2006 |
| WO | 2009/097325 A1 | 8/2009 |

OTHER PUBLICATIONS

Cai, M. et al., Single chain Fv antibody against angiopoietin-2 inhibits VEGF-induced endothelial cell proliferation and migration in vitro, Biochemical and Biophysical Research Communications, 2003, vol. 309 (4): 946-951.
Hu, B. et al., Angiopoietin-2: development of inhibitors for cancer therapy, Curr Oncol Rep., 2009, vol.11(2):111-116.
Oliner, J. et al., Suppression of angiogenesis and tumor growth by selective inhibition of angiopoietin-2, Cancer Cell., 2004, vol. 6(5):507-516.
Wang, H-L. et al., "Effects of anti-angiopoietin-2 antibody on vascularization of an implanted model of human colonic carcinoma on chick embryo", Chinese J. Gastrointestinal Surgery 10 (3): 278. English abstract only (abstract retrieved from STN database accession No. NLM17520390 (May 3, 2007).
EP Extended Search Report for Application No. 10194248.0-2406 dated May 17, 2011.

*Primary Examiner* — Lynn Bristol
(74) *Attorney, Agent, or Firm* — Leydig, Voit & Mayer, Ltd.

(57) ABSTRACT

An antibody specifically binding to angiopoietin-2, and antigen-binding fragments thereof, and a use thereof are disclosed.

14 Claims, 7 Drawing Sheets

| TREATMENT GROUP | AVERAGE TUMOR MASS (g) |
|---|---|
| 1. CONTROL | 1.4 |
| 2. SAIT-Ang-2-5 (0.4 mg/kg) | 1.1 |
| 3. SAIT-Ang-2-5 (2 mg/kg) | 0.8 |
| 4. SAIT-Ang-2-6 (0.4 mg/kg) | 0.9 |
| 5. SAIT-Ang-2-6 (2 mg/kg) | 0.6 |

```
                        SEQUENCE LISTING

<160> NUMBER OF SEQ ID NOS: 20

<210> SEQ ID NO 1
<211> LENGTH: 5
<212> TYPE: PRT
<213> ORGANISM: Artificial Sequence
<220> FEATURE:
<223> OTHER INFORMATION: heavy chain CDR1 of monoclonal antibody
      SAIT-Ang-2-5

<400> SEQUENCE: 1

Asn Phe Gly Met His
 1               5

<210> SEQ ID NO 2
<211> LENGTH: 17
<212> TYPE: PRT
<213> ORGANISM: Artificial Sequence
<220> FEATURE:
<223> OTHER INFORMATION: heavy chain CDR2 of monoclonal antibody
      SAIT-Ang-2-5

<400> SEQUENCE: 2

Tyr Ile Ser Ser Gly Ser Asp Thr Ile Tyr Tyr Ala Asp Thr Val Lys
 1               5                  10                  15

Gly

<210> SEQ ID NO 3
<211> LENGTH: 20
<212> TYPE: PRT
<213> ORGANISM: Artificial Sequence
<220> FEATURE:
<223> OTHER INFORMATION: heavy chain CDR3 of monoclonal antibody
      SAIT-Ang-2-5

<400> SEQUENCE: 3

Glu Ser Thr Met Ile Thr Met Gly Tyr Val Leu Asp Tyr Trp Gly Gln
 1               5                  10                  15

Gly Thr Ser Val
            20

<210> SEQ ID NO 4
<211> LENGTH: 122
<212> TYPE: PRT
<213> ORGANISM: Artificial Sequence
```

-continued

```
<220> FEATURE:
<223> OTHER INFORMATION: heavy chain variable region of monoclonal
      antibody SAIT-Ang-2-5

<400> SEQUENCE: 4

Asp Val Gln Leu Val Glu Ser Gly Gly Gly Leu Ala Gln Pro Gly Gly
 1               5                  10                  15

Ser Arg Lys Leu Ser Cys Ala Ala Ser Gly Phe Thr Phe Ser Asn Phe
            20                  25                  30

Gly Met His Trp Val Arg Gln Ala Pro Glu Lys Gly Leu Asp Trp Val
        35                  40                  45

Ala Tyr Ile Ser Ser Gly Ser Asp Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Glu Ser Thr Met Ile Thr Met Gly Tyr Val Leu Asp Tyr Trp
           100                 105                 110

Gly Gln Gly Thr Ser Val Thr Val Ser Ser
       115                 120

<210> SEQ ID NO 5
<211> LENGTH: 11
<212> TYPE: PRT
<213> ORGANISM: Artificial Sequence
<220> FEATURE:
<223> OTHER INFORMATION: light chain CDR1 of monoclonal antibody
      SAIT-Ang-2-5

<400> SEQUENCE: 5

Leu Ala Ser Gln Thr Ile Gly Thr Trp Leu Ala
 1               5                  10

<210> SEQ ID NO 6
<211> LENGTH: 7
<212> TYPE: PRT
<213> ORGANISM: Artificial Sequence
<220> FEATURE:
<223> OTHER INFORMATION: light chain CDR2 of monoclonal antibody
      SAIT-Ang-2-5

<400> SEQUENCE: 6

Ala Ala Thr Ser Leu Ala Asp
 1               5

<210> SEQ ID NO 7
<211> LENGTH: 12
<212> TYPE: PRT
<213> ORGANISM: Artificial Sequence
<220> FEATURE:
<223> OTHER INFORMATION: light chain CDR3 of monoclonal antibody
      SAIT-Ang-2-5

<400> SEQUENCE: 7

Gln Gln Leu Tyr Ser Ile Pro Leu Thr Ile Gly Ala
 1               5                  10

<210> SEQ ID NO 8
<211> LENGTH: 107
<212> TYPE: PRT
<213> ORGANISM: Artificial Sequence
<220> FEATURE:
<223> OTHER INFORMATION: light chain variable region of monoclonal
      antibody SAIT-Ang-2-5
```

<400> SEQUENCE: 8

Asp Ile Gln Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Thr Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Leu Lys Ile Ser Leu Gln Ala
65                  70                  75                  80

Glu Asp Phe Val Ser Tyr Tyr Cys Gln Gln Leu Tyr Ser Ile Pro Leu
                85                  90                  95

Thr Ile Gly Ala Gly Thr Lys Leu Glu Leu Lys
            100                 105

<210> SEQ ID NO 9
<211> LENGTH: 5
<212> TYPE: PRT
<213> ORGANISM: Artificial Sequence
<220> FEATURE:
<223> OTHER INFORMATION: heavy chain CDR1 of monoclonal antibody
      SAIT-Ang-2-6

<400> SEQUENCE: 9

Asn Tyr Leu Met His
1               5

<210> SEQ ID NO 10
<211> LENGTH: 17
<212> TYPE: PRT
<213> ORGANISM: Artificial Sequence
<220> FEATURE:
<223> OTHER INFORMATION: heavy chain CDR2 of monoclonal antibody
      SAIT-Ang-2-6

<400> SEQUENCE: 10

Asn Ile Tyr Pro Gly Ser Gly Ala Thr Asn Tyr Asp Glu Lys Phe Lys
1               5                   10                  15

Ser

<210> SEQ ID NO 11
<211> LENGTH: 17
<212> TYPE: PRT
<213> ORGANISM: Artificial Sequence
<220> FEATURE:
<223> OTHER INFORMATION: heavy chain CDR3 of monoclonal antibody
      SAIT-Ang-2-6

<400> SEQUENCE: 11

Asp Asp Tyr Asp Gly Ser Trp Phe Ala Tyr Trp Gly Gln Gly Thr Leu
1               5                   10                  15

Val

<210> SEQ ID NO 12
<211> LENGTH: 119
<212> TYPE: PRT
<213> ORGANISM: Artificial Sequence
<220> FEATURE:
<223> OTHER INFORMATION: heavy chain variable region of monoclonal
      antibody SAIT-Ang-2-6

<400> SEQUENCE: 12

Gln Val Gln Leu Gln Gln Pro Gly Ser Glu Leu Val Arg Pro Gly Thr
1               5                   10                  15

Ser Val Lys Leu Ser Cys Lys Ala Ser Gly Tyr Thr Phe Thr Asn Tyr
            20                  25                  30

Leu Met His Trp Val Lys Gln Arg Pro Gly Gln Gly Leu Glu Trp Ile
        35                  40                  45

Gly Asn Ile Tyr Pro Gly Ser Gly Ala Thr Asn Tyr Asp Glu Lys Phe
    50                  55                  60

Lys Ser Lys Ala Thr Leu Thr Val Asp Ile Ser Ser Thr Ala Tyr
65                  70                  75                  80

Met Gln Leu Ile Ser Leu Thr Ser Glu Asp Ser Ala Val Tyr Tyr Cys
                85                  90                  95

Thr Arg Asp Asp Tyr Asp Gly Ser Trp Phe Ala Tyr Trp Gly Gln Gly
            100                 105                 110

Thr Leu Val Thr Val Ser Ala
        115

<210> SEQ ID NO 13
<211> LENGTH: 17
<212> TYPE: PRT
<213> ORGANISM: Artificial Sequence
<220> FEATURE:
<223> OTHER INFORMATION: light chain CDR1 of monoclonal antibody
      SAIT-Ang-2-6

<400> SEQUENCE: 13

Lys Ser Ser Gln Ser Leu Leu Ile Ser Gly Asn Gln Lys Asn Phe Leu
1               5                   10                  15

Ala

<210> SEQ ID NO 14
<211> LENGTH: 7
<212> TYPE: PRT
<213> ORGANISM: Artificial Sequence
<220> FEATURE:
<223> OTHER INFORMATION: light chain CDR2 of monoclonal antibody
      SAIT-Ang-2-6

<400> SEQUENCE: 14

Gly Ala Ser Thr Arg Asp Ser
1               5

<210> SEQ ID NO 15
<211> LENGTH: 12
<212> TYPE: PRT
<213> ORGANISM: Artificial Sequence
<220> FEATURE:
<223> OTHER INFORMATION: light chain CDR3 of monoclonal antibody
      SAIT-Ang-2-6

<400> SEQUENCE: 15

Gln Asn Asp His Ser Tyr Pro Leu Thr Phe Gly Thr
1               5                   10

<210> SEQ ID NO 16
<211> LENGTH: 113
<212> TYPE: PRT
<213> ORGANISM: Artificial Sequence
<220> FEATURE:
<223> OTHER INFORMATION: light chain variable region of monoclonal
      antibody SAIT-Ang-2-6

<400> SEQUENCE: 16

Asp Ile Val Met Thr Gln Ser Pro Ser Ser Leu Ser Val Ser Ala Gly
1               5                   10                  15

Glu Lys Val Thr Met Thr Cys Lys Ser Ser Gln Ser Leu Leu Ile Ser
            20                  25                  30

Gly Asn Gln Lys Asn Phe Leu Ala Trp Tyr Gln Gln Lys Pro Gly Gln
        35                  40                  45

Pro Pro Lys Leu Leu Ile Tyr Gly Ala Ser Thr Arg Asp Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp His Ser Tyr Pro Leu Thr Phe Gly Thr Gly Thr Lys Leu Glu Leu
            100                 105                 110

Lys

<210> SEQ ID NO 17
<211> LENGTH: 366
<212> TYPE: DNA
<213> ORGANISM: Artificial Sequence
<220> FEATURE:
<223> OTHER INFORMATION: heavy chain variable region of monoclonal
      antibody SAIT-Ang-2-5

<400> SEQUENCE: 17
gatgtgcagc tggtggagtc tgggggaggc ttagcgcagc ctggagggtc ccggaaactc      60
tcctgtgcag cctctggatt cactttcagt aactttggaa tgcactgggt tcgtcaggct     120
ccagagaagg gactgactg gtcgcatac attagtagtg gcagtgatac catctactat      180
gcagacacag tgaagggccg attcaccatc tccagagaca tcccaagaa caccctgttc      240 ctgcaaatga ccagtctaag gtctgaggac acggccatgt attactgtgc aagagaatct     300
actatgatta cgatgggcta tgttttggac tactggggtc aaggaacctc agtcaccgtc     360
tcctca                                                                 366

<210> SEQ ID NO 18
<211> LENGTH: 321
<212> TYPE: DNA
<213> ORGANISM: Artificial Sequence
<220> FEATURE:
<223> OTHER INFORMATION: light chain variable region of monoclonal
      antibody SAIT-Ang-2-5

<400> SEQUENCE: 18
gacattcaga tgacccagtc tcctgcctcc cagtctgcat ctctgggaga aagtgtcacc      60
atcacatgcc tggcaagtca gaccattggt acatggttag catggtatca gcagaaacca     120
gggaaatctc cgcagctcct gatttatgct gcaaccagct ggcagatgg gtcccatca      180 aggttcagtg gtagtggatc tggcacaaaa ttttctttga agatcagcag cctacaggct     240
gaagattttg taagttatta ctgtcaacaa ctttacagta ttccgctcac gatcggtgct     300
gggaccaagc tggagctgaa a                                                321

<210> SEQ ID NO 19
<211> LENGTH: 357
<212> TYPE: DNA
<213> ORGANISM: Artificial Sequence
<220> FEATURE:
<223> OTHER INFORMATION: heavy chain variable region of monoclonal
      antibody SAIT-Ang-2-6

```
-continued

<400> SEQUENCE: 19
caggtccaac tgcagcaacc tgggtctgag ctggtgaggc ctggaacttc agtgaagctg      60
tcctgcaagg cttctggcta cacattcacc aactacttga tgcactgggt gaagcagagg     120
cctggacaag gccttgagtg gattggaaat atttatcctg gtagtggtgc tactaactac     180
gatgagaagt tcaagagtaa ggccacactg actgtagaca tatcctccag cacagcctac     240
atgcagctca tcagcctgac atctgaggac tctgcggtct attactgtac aagagatgat     300
tacgacgggt cctggtttgc ttactgggc caagggactc tggtcactgt ctctgca        357

<210> SEQ ID NO 20
<211> LENGTH: 339
<212> TYPE: DNA
<213> ORGANISM: Artificial Sequence
<220> FEATURE:
<223> OTHER INFORMATION: light chain variable region of monoclonal
      antibody SAIT-Ang-2-6

<400> SEQUENCE: 20
gacattgtga tgacacagtc tccatcctcc ctgagtgtgt cagcaggaga gaaggtcact      60
atgacctgta gtccagtca gagtctgtta atcagtggaa atcaaaagaa cttcttggcc     120
tggtaccagc agaaaccagg acagcctcct aaattgttaa tctacggggc atccactagg     180
gattctgggg tccctgatcg cttcacaggc agtggatctg gaaccgattt cactcttacc     240
atcagcagtg tgcaggctga agacctggca gtttattact gtcagaatga tcatagttat     300
ccgctcacgt tcggtactgg gaccaagctg gagctgaaa                           339
```

ANTIBODY SPECIFICALLY BINDING TO ANGIOPOIETIN-2 AND USE THEREOF

CROSS-REFERENCE TO RELATED APPLICATIONS

This application claims the benefit of Korean Patent Application No. 10-2009-0125035, filed Dec. 15, 2009, and all the benefits accruing therefrom under 35 U.S.C. §119, the disclosure of which is incorporated herein in its entirety by reference.

BACKGROUND

1. Field

The present disclosure relates to antibodies specifically binding to angiopoietin-2, fragments thereof, and use of the antibodies.

2. Description of the Related Art

Angiogenesis is a process involving the growth of new blood vessels from pre-existing vessels. Angiogenesis plays a vital role in the formation of organs, normal biological growth, and wound healing. In addition, abnormal angiogenesis is known to be an important contributor to diseases such as development and metastasis of tumors, age-related macular degeneration, diabetic retinopathy, psoriasis, rheumatoid arthritis, and chronic inflammation.

Since development and metastasis of tumors depend on angiogenesis, it has been suggested that anti-angiogenesis drugs would be novel anti-cancer drugs. Therefore research into the mechanism of angiogenesis has been conducted to develop new anti-cancer drugs. One of the target proteins is angiopoietin. Angiopoietin, an angiogenesis factor, is known to participate in blood vessel development and angiogenesis after birth. Examples of identified angiopoietins include angiopoietin-1, angiopoietin-2, angiopoietin-3, and angiopoietin-4.

Angiopoietins, in concert with vascular endothelial growth factor (VEGF), are a family of growth factors that modulate tumor angiogenesis mediated through the Tie2 receptor, which is highly expressed in growing blood endothelial cells. Angiopoietin-2 (Ang-2) binds to Tie2. Among the various angiopoietins, Angiopoietin-2 (Ang-2) when alone, regresses blood vessels. However, the blood vessel regression causes hypoxia within the cancer tissue, which is an environment in which angiogenesis is possible. Under such condition, expression of VEGF is increased, and new blood vessels are formed.

Preclinical and clinical trials are being conducted on various kinds of the currently available angiogenesis inhibiting agents. Although a few antagonists of the biological activity of angiopoietin-2 are known, such as an antibody specifically binding Ang-2 which has been shown to reduce tumor angiogenesis, and growth in some tumor models, there is a need for additional angiopoietin-2 antagonists displaying anti-cancer and/or anti-angiogenesis effects.

SUMMARY

Provided are antibodies specifically binding to angiopoietin-2, or antigen binding fragments thereof.

Provided are polynucleotides encoding a heavy chain variable region and a light chain variable region of an antibody specifically binding to angiopoietin-2.

Provided are recombinant vectors including polynucleotides that encode a light chain variable region and a heavy chain variable region of an antibody specifically binding to angiopoietin-2 and host cells transformed with the recombinant vectors.

Provided is a composition including an antibody specifically binding to angiopoietin-2, or antigen binding fragment thereof. In an embodiment, the composition further includes a pharmaceutically acceptable excipient.

Provided is a method for preventing or treating an angiogenesis-related disease or cancer. In an embodiment, the method includes administering a therapeutically effective amount of an antibody specifically binding to angiopoietin-2, or antigen binding fragment thereof; to a subject having an angiogenesis-related disease or cancer.

Also provided is a method of detecting the presence or amount of angiopoietin-2 present in a sample. In an embodiment, the method includes contacting a sample with an antibody specifically binding to angiopoietin-2, or an antigen binding fragment thereof; and detecting complex formation between the antibody and angiopoietin-2 thereby detecting the presence or amount of angiopoietin-2 in the sample.

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Figure 1:
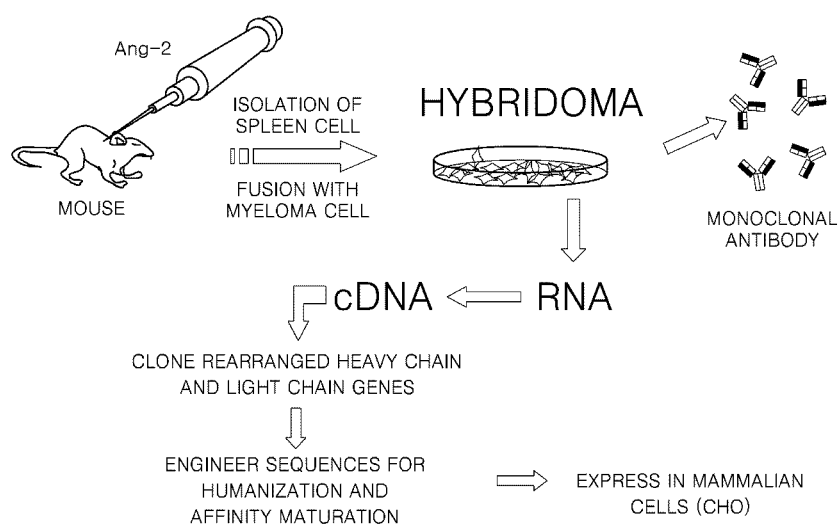
FIG. 1 is a schematic diagram showing the process of producing monoclonal antibodies SAIT-Ang-2-5 and SAIT-Ang-2-6 and humanized chimeric antibodies including the heavy and light chain variable regions thereof, according to an embodiment of the present invention.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

According to an embodiment of the present invention, there is provided a monoclonal antibody that is produced by a hybridoma cell having accession number KCLRF-BP-00221, and that specifically binds angiopoietin-2.

According to an embodiment of the present invention, there is provided a monoclonal antibody that is produced by a hybridoma cell having accession number KCLRF-BP-00222, and that specifically binds angiopoietin-2.

Angiopoietin-2 is a type of angiopoietin, which is an angiogenic factor. The term "angiopoietin-2" used herein refers to a protein acting as a ligand of the Tie-2 receptor which is specifically expressed in vascular endothelial cells. Binding of angiopoietin-2 to the Tie-2 receptor induces instability and vessel regression of vascular endothelial cells. In particular, angiogenesis in tumor tissue is performed in such a way that vessel regression caused by angiopoietin-2 causes a hypoxic environment within the tumor tissue, and under such conditions, the expression of angiogenic growth factors, such as a vascular endothelial cell growth factor (VEGF) is increased, and new blood vessels are formed.

The term "specifically binding" or "specifically recognized" herein means that an antibody exhibits appreciable affinity for an antigen and, preferably, does not exhibit significant crossreactivity. "Appreciable" binding affinity includes binding with an affinity of at least $10^6$ $M^{-1}$, specifically at least $10^7$ $M^{-1}$, more specifically at least $10^8$ $M^{-1}$, yet more specifically at least $10^9$ $M^{-1}$, or even yet more specifically at least $10^{19}$ $M^{-1}$. A binding affinity can also be indicated as a range of affinities, for example, $10^6$ $M^{-1}$ to $10^{19}$ $M^{-1}$, specifically $10^7$ $M^{-1}$ to $10^{19}$ $M^{-1}$, more specifically $10^8$ $M^{-1}$ to $10^{19}$ $M^{-1}$. An antibody that "does not exhibit significant crossreactivity" is one that will not appreciably bind to an undesirable entity (e.g., an undesirable proteinaceous entity). An antibody specific for a particular epitope will, for example, not significantly crossreact with remote epitopes on the same protein or peptide. Specific binding can be determined according to any art-recognized means for determining such binding. In some embodiments, specific binding is determined according to Scatchard analysis and/or competitive binding assays.

The structure of a naturally occurring, intact antibody, or immunoglobulin (Ig), includes four polypeptides: two full-length light chains and two full-length heavy chains, in which each light chain is linked to a heavy chain by disulfide bonds (SS-bond). Each heavy chain has a constant region and a variable region. Similarly, each light chain has a constant region and a variable region. The heavy chain constant region can be classified as a gamma (γ), mu (μ), alpha (α), delta (δ), or epsilon (ε) isotype; additionally, there are several subclasses: gamma 1 (γ1), gamma 2(γ2), gamma 3(γ3), gamma 4(γ4), alpha 1(α1), or alpha 2(α2). The light chain constant region is either a kappa (κ) or a lambda (λ) isotype. The variable regions differ in sequence among antibodies and are used in the binding and specificity of a given antibody to its particular antigen.

The term "monoclonal antibody" used herein refers to all antibodies derived from a single cell clone. A monoclonal antibody has binding specificity to only a single antigen, and also has affinity for only a specific epitope of the antigen.

A hybridoma cell may be prepared using a method known in the art. For example, a hybridoma cell may be prepared by immunizing an animal with the immunogen, angiopoietin-2, fusing antibody-producing B cells derived from the immunized animal with myeloma cells to prepare hybridomas, and selecting the hybridomas that produce antibodies that specifically bind angiopoietin-2. The animal that is immunized may be a mouse, a goat, a sheep, a guinea pig, a rat, or a rabbit.

Immunization may be performed using a method known in the art. For example, mice are immunized by emulsifying 1-100 μg immunogen per dose with an antigen adjuvant, such as a saline solution and/or Freund's adjuvant, in the same volume as that of the immunogen and administering the immunogen to the mice via subcutaneous or intraperitoneal injection 2 to 6 times at intervals of 2 to 5 weeks. Three to 5 days after the final immunization of the mice, the spleen or lymphatic gland is taken out, and B cells contained in this tissue are fused with myeloma cells using a cell fusion method known in the art in the presence of a fusion facilitator. The fusion facilitator may be polyethylene glycol (PEG). The myeloma cells may be mouse-derived cells, such as P3U1, NS-1, P3×63.Ag 8.653, and Sp2/0-Ag14, or rat-derived cells, such as AG1 and AG2, but are not limited thereto. For example, cell fusion may be performed by mixing B cells and myeloma cells at a ratio of 1:1 to 10:1, adding 10-80% of PEG having a molecular weight of 1,000-6,000 thereto, and incubating the result at a temperature of about 30 to about 37° C. for about 1 to about 10 minutes. In addition, a hybridoma, which produces a monoclonal antibody specifically binding angiopoietin-2, may be selected by culturing the hybridoma in a selective medium, such as aminopterin thymidine (HAT) medium in which only hybridoma survives, and measuring the antibody activity in the hybridoma culture supernatant using an enzyme-linked immunosorbent assay (ELISA) method. Finally, selecting a single hybridoma clone, which produces a monoclonal antibody specifically binding angiopoietin-2, may involve a repetitive cloning technique such as limiting dilutions.

The monoclonal antibody may be an $IgG_1$, $IgG_2$, $IgG_3$, $IgG_4$, IgM, IgE, $IgA_1$, $IgA_5$, or IgD-type antibody, for example, an $IgG_1$-type antibody. In addition, the light chain constant region of the monoclonal antibody may be of either λ or κ type. The angiopoietin-2 used as an antigen may be derived from humans or mice.

According to an embodiment of the present invention, there is provided an antibody that specifically binds angiopoietin-2 and that has a heavy chain variable region including at least one heavy chain complementarity determining region (CDR) amino acid sequence selected from the group consisting of SEQ ID NO:1, SEQ ID NO:2, and SEQ ID NO:3, and a light chain variable region including at least one light chain CDR amino acid sequence selected from the group consisting of SEQ ID NO:5, SEQ ID NO:6, and SEQ ID NO:7. In some embodiments, the antibody is an antigen binding fragment of an intact antibody. In an embodiment, the heavy chain variable region comprises CDR amino acid sequences SEQ ID NO:1, SEQ ID NO:2, and SEQ ID NO:3. In an embodiment, the light chain variable region comprises CDR amino acid sequences SEQ ID NO:5, SEQ ID NO:6, and SEQ ID NO:7.

In an embodiment, the heavy chain variable region may have the amino acid sequence of SEQ ID NO: 4, and the light chain variable region may have the amino acid sequence of SEQ ID NO: 8.

According to an embodiment of the present invention, there is provided an antibody that specifically binds angiopoietin-2 and that has a heavy chain variable region including at least one heavy chain CDR amino acid sequence selected from the group consisting of SEQ ID NO:9, SEQ ID NO:10, and SEQ ID NO:11, and a light chain variable region including at least one light chain CDR amino acid sequence selected from the group consisting of SEQ ID NO:13, SEQ ID NO:14, and SEQ ID NO:15. In some embodiments the antibody is an antigen binding fragment of an intact antibody. In an embodiment, the heavy chain variable region comprises CDR amino acid sequences SEQ ID NO: 9, SEQ ID NO: 10, and SEQ ID NO: 11. In an embodiment, the light chain variable region comprises CDR amino acid sequences SEQ ID NO: 13, SEQ ID NO: 14, and SEQ ID NO: 15.

In an embodiment, the heavy chain variable region may have the amino acid sequence of SEQ ID NO: 12, and the light chain variable region may have the amino acid sequence of SEQ ID NO: 16.

The term "antibody" used herein includes intact antibodies and also antigen binding fragments of intact antibody molecules, i.e., antibody fragments having antibody-like specific binding to an antigen, such as angiopoietin-2.

The term "heavy chain" used herein includes a full-length heavy chain including a variable region ($V_H$) having amino acid sequences that contribute to the specificity for antigen binding and a constant region having three constant domains ($C_{H1}$, $C_{H2}$, and $C_{H3}$), and fragments thereof. In addition, the term "light chain" used herein is understood to include a full-length light chain including a variable region ($V_L$) having amino acid sequences that contribute to the specificity for antigen binding and a constant region ($C_L$), and fragments thereof.

The term "complementarity determining region (CDR)" used herein refers to an amino acid sequence found in the variable region of a heavy chain or a light chain of an immunoglobulin. The CDRs determine the specificity of an antibody and may provide a contact residue for binding to a specific epitope of the antigen. The heavy chain and the light chain may respectively include three CDRs (CDR1 (CDRH1 & CDRL1), CDR2 (CDRH2 & CDRL2), and CDR3 (CDRH3 & CDRL3)). Four framework regions, which have more highly conserved amino acid sequences than the CDRs, separate the CDR regions in the $V_H$ or $V_L$.

The term "antigen binding fragment(s)" used herein refers to fragments of an intact immunoglobulin, including some or all of the antigen binding regions and having the ability to specifically bind to the antigen of the intact immunoglobulin. For example, the antigen binding fragment may be a F(ab')$_2$ fragment, a Fab' fragment, a Fab fragment, a Fv fragment, or a scFv fragment, but is not limited thereto. A Fab fragment has the variable regions of a light chain and a heavy chain, the constant regions of the light chain, and the first constant region $C_{H1}$ of the heavy chain, and has one antigen binding site. A Fab' fragment is different from Fab in that Fab' additionally has the hinge region of the heavy chain, including at least one cysteine residue at the C-terminal of the heavy chain $C_{H1}$ region. A F(ab')$_2$ fragment is produced when cysteine residues of the Fab' fragment are joined by a disulfide bond at the hinge region. A Fv fragment is the minimal antibody fragment, having only the heavy chain variable regions and the light chain variable regions, and a recombinant technique for producing the Fv fragment is well known in the art. Two-chain Fv fragments may have a structure in which the heavy chain variable regions are linked to the light chain variable regions by a non-covalent bond. Single-chain Fv fragments generally may have a dimer structure as in the two-chain Fv fragments in which the heavy chain variable regions are covalently bound to the light chain variable regions via a peptide linker or the heavy and light chain variable regions are directly linked to each other at the C-terminal ends thereof. An antigen binding fragment may be obtained using a protease (for example, a whole antibody can be digested with papain to obtain Fab fragments, or can be digested with pepsin to obtain F(ab')$_2$ fragments), or may be prepared by a genetic recombinant technique.

The antibody may be a monoclonal antibody, a bispecific antibody, a non-human antibody, a human antibody, a humanized antibody, a chimeric antibody, a single chain Fvs (scFV) fragment, a single chain antibody, a Fab fragment, a F(ab') fragment, a disulfide-bond Fvs (sdFV) fragment, an anti-idiotype (anti-Id) antibody, and epitope-binding fragments of these antibodies, but is not limited thereto.

The antibody may be a humanized antibody or a human antibody. A humanized antibody of a non-human species, for example, mice, may be a chimeric immunoglobulin including minimal sequences derived from the immunoglobulin of mice, chains of the immunoglobulin, fragments thereof, and may be, for example, Fv, Fab, Fab', F(ab')$_2$, or other antigen-binding subsequences of the antibody.

A non-human antibody is humanized using a method known in the art. In general, a humanized antibody has at least one amino acid residue introduced from a non-human donor. For example, humanization of a non-human antibody may be performed by replacing residues in a CDR of the recipient with residues from a corresponding CDR of a non-human species, such as a mouse, rat, rabbit, or non-human primate, having the desired specificity, affinity, and capacity. In some instances, framework region (FR) residues of the human immunoglobulin are replaced by corresponding non-human residues.

A human antibody refers to an antibody having amino acid sequences of the variable and constant regions of the heavy and light chains derived from humans. A human antibody may be produced using various techniques known in the art, for example, using a phage display library, a genetic recombinant technique, or cell engineering.

The effector regions of a human antibody may more successfully interact with other components of the human immune system. For example, the human immune system does not recognize a human antibody as foreign material, and thus, the immune reaction against a human antibody introduced into a human may be less active than the immune reaction against full-length non-human antibodies, chimeric antibodies, or fragments thereof, introduced into a human. Moreover, a human antibody into a human has substantially the same half-life as that of endogenous human antibodies, and thus, doses and frequency of administration may be reduced.

The term "chimeric" used herein indicates that an antibody or the antigen binding site of an antibody (paratope) includes sequences derived from two different species.

The antibody specifically binding to angiopoietin-2, or the antigen binding fragments thereof, may include variants of amino acid sequences disclosed herein within a range retaining the ability to specifically recognize angiopoietin-2. For example, to enhance the binding affinity and/or other biological properties of the antibody, the amino acid sequences of the antibody may be mutated. For example, such mutations include deletion, insertion, and/or substitution of amino acid sequence residues of the antibody. An amino acid mutation is made based on the relative similarity of the amino acid side chain substituents, for example, with respect to hydrophobic properties, hydrophilic properties, charges, or sizes. For example, arginine, lysine, and histidine are each a positively charged residue; alanine, glycine, and serine have a similar size; and phenylalanine, tryptophan, and tyrosine have a similar shape. Therefore, based on the considerations described above, arginine, lysine, and histidine may be biological functional equivalents; alanine, glycine, and serine may be biological functional equivalents; and phenylalanine, tryptophan, and tyrosine may be biological functional equivalents.

Amino acid substitution in a protein in which the activity of the molecule is not completely changed is well known in the art. Typical substitutions include Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly substitutions. Considering mutations with biologically equivalent activity, an antibody specifically binding to angiopoietin-2 or the antigen-binding fragments thereof may also include sequences substantially identical to sequences disclosed herein. In this regard, a substantially identical amino acid sequence may be a sequence with at least 60% homology, at least 70% homology, at least 80% homology, or at least 90% homology to a sequence disclosed herein, when the amino acid sequences are aligned to correspond to each other as much as possible. The aligned amino acid sequences are analyzed using an algorithm known in the art. Alignment methods for sequence comparison are well known to one of ordinary skill in the art. For example, a sequence analysis program available on the Internet at the NCBI Basic Local Alignment Search Tool (BLAST) home page, such as blastp, blastx, tblastn, or tblastx, may be used.

According to an embodiment of the present invention, there is provided a polynucleotide encoding the heavy chain variable region of an antibody specifically binding to angiopoietin-2 having an amino acid sequence of SEQ ID NO: 4.

In another embodiment, an isolated polynucleotide encodes an antibody heavy chain variable region comprising at least one heavy chain complementarity determining region (CDR) amino acid sequence selected from the group consisting of SEQ ID NO: 1, SEQ ID NO: 2, and SEQ ID NO: 3.

The polynucleotide may have a nucleotide sequence of SEQ ID NO: 17.

According to an embodiment of the present invention, there is provided a polynucleotide encoding a light chain variable region of an antibody specifically binding to angiopoietin-2 having an amino acid sequence of SEQ ID NO: 8.

In another embodiment, an isolated polynucleotide encodes an antibody light chain variable region comprising at least one light chain complementarity determining region (CDR) amino acid sequence selected from the group consisting of SEQ ID NO: 5, SEQ ID NO: 6, and SEQ ID NO: 7.

The polynucleotide may have a nucleotide sequence of SEQ ID NO: 18.

According to an embodiment of the present invention, there is provided a polynucleotide encoding a heavy chain variable region of an antibody specifically binding to angiopoietin-2 having an amino acid sequence of SEQ ID NO: 12.

In an embodiment, an isolated polynucleotide encodes an antibody heavy chain variable region comprising at least one heavy chain complementarity determining region (CDR) amino acid sequence selected from the group consisting of SEQ ID NO: 9, SEQ ID NO: 10, and SEQ ID NO: 11.

The polynucleotide may have a nucleotide sequence of SEQ ID NO: 19.

According to an embodiment of the present invention, there is provided a polynucleotide encoding a light chain variable region of an antibody specifically binding to angiopoietin-2 having an amino acid sequence of SEQ ID NO: 16.

In an embodiment, an isolated polynucleotide encodes an antibody light chain variable region comprising at least one light chain complementarity determining region (CDR) amino acid sequence selected from the group consisting of SEQ ID NO: 13, SEQ ID NO: 14, and SEQ ID NO: 15.

The polynucleotide may have a nucleotide sequence of SEQ ID NO: 20.

The term "polynucleotide" used herein refers to a polymer of deoxyribonucleotide or ribonucleotide that exists as a single-stranded or double-stranded form. The polynucleotide includes RNA genome sequences, DNA (gDNA and cDNA), and RNA sequences transcribed therefrom, and includes analogues of natural polynucleotides, unless specifically mentioned.

The polynucleotide also includes nucleotide sequences encoding the amino acid sequences of the heavy and light chain variable regions of an antibody disclosed herein, and nucleotide sequences complementary thereto. The complementary sequences include completely complementary sequences and substantially complementary sequences. For example, substantially complementary sequences are sequences that may be hybridized with nucleotide sequences encoding the amino acid sequences of the heavy or light chain variable regions of an antibody disclosed herein under stringent conditions known in the art. Specifically, stringent conditions mean, for example, hybridization to DNA in 6×SSC at about 45° C., followed by one or more washes in 0.2×SSC/0.1% SDS at about 50° C.-65° C.

In addition, the nucleotide sequences encoding the amino acid sequences of the heavy and light chain variable regions may be mutated. The mutations include addition, deletion or substitution of nucleotides, and non-conservative or conservative substitution of amino acids. A polynucleotide encoding the amino acid sequence of a heavy or light chain variable region of an antibody specifically binding to the angiopoietin-2 is understood to include nucleotide sequences substantially identical to the nucleotide sequences described above. The substantially identical sequences may be sequences with at least 80% homology, at least 90% homology, or at least 95% homology to the nucleotide sequences, when the nucleotide sequences are aligned to correspond to each other as much as possible. The aligned nucleotide sequences are analyzed using an algorithm known in the art. Examples of sequence analysis programs are available on the Internet at the NCBI Basic Local Alignment Search Tool (BLAST) home page, for example, blastn.

According to an embodiment of the present invention, there is provided a recombinant vector. In an embodiment, the recombinant vector includes a polynucleotide encoding a heavy chain variable region having an amino acid sequence of SEQ ID NO: 4 or a polynucleotide encoding a light chain variable region having an amino acid sequence of SEQ ID NO: 8.

In some embodiments, the recombinant vector includes a polynucleotide encoding a heavy chain variable region having an amino acid sequence of SEQ ID NO: 4 and a polynucleotide encoding a light chain variable region having an amino acid sequence of SEQ ID NO: 8.

In an embodiment, the recombinant vector comprises an isolated polynucleotide encoding an antibody heavy chain variable region comprising at least one heavy chain complementarity determining region (CDR) amino acid sequence selected from the group consisting of SEQ ID NO: 1, SEQ ID NO: 2, and SEQ ID NO: 3; or an isolated polynucleotide encoding an antibody light chain variable region comprising at least one light chain complementarity determining region (CDR) amino acid sequence selected from the group consisting of SEQ ID NO: 5, SEQ ID NO: 6, and SEQ ID NO: 7.

In an embodiment, the recombinant vector comprises an isolated polynucleotide encoding an antibody heavy chain variable region comprising at least one heavy chain complementarity determining region (CDR) amino acid sequence selected from the group consisting of SEQ ID NO: 9, SEQ ID NO: 10, and SEQ ID NO: 11; or an isolated polynucleotide encoding an antibody light chain variable region comprising at least one light chain complementarity determining region (CDR) amino acid sequence selected from the group consisting of SEQ ID NO: 13, SEQ ID NO: 14, and SEQ ID NO: 15.

According to an embodiment of the present invention, there is provided a recombinant vector including a polynucleotide encoding a heavy chain variable region having an amino acid sequence of SEQ ID NO: 12 or a polynucleotide encoding a light chain variable region having an amino acid sequence of SEQ ID NO: 16. In some embodiments, the recombinant vector includes a polynucleotide encoding a heavy chain variable region having an amino acid sequence of SEQ ID NO: 12 and a polynucleotide encoding a light chain variable region having an amino acid sequence of SEQ ID NO: 16.

The term "vector" used herein refers to a polynucleotide as a means of transporting a target gene and expressing the target gene in a host cell. For example, the vector may be a plasmid vector, a cosmid vector, or a viral vector, such as a bacteriophage vector, an adenovirus vector, a retrovirus vector, and an adeno-associated virus vector. The recombinant vector may be prepared by manipulating a plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (for example, λgt4λB, λ-Charon, λΔz1, and M13), or a virus (for example, CMV and SV40) known in the art.

In the recombinant vector, the polynucleotides encoding the amino acid sequences of the heavy and light chain variable regions may be operatively linked to a promoter. The term "operatively linked" used herein means a functional linkage between a nucleotide expression regulating sequence (for example, a promoter sequence) and other nucleotide sequences. Thus, the nucleotide expression regulating sequence may regulate the transcription and/or translation of the other nucleotide sequences.

The recombinant vector may be constructed for cloning or expression. For example, a vector for expression may be a vector known in the art for expressing a foreign protein in a plant, animal, or microorganism. The recombinant vector may be constructed using various methods known in the art.

The recombinant vector may be constructed for use in prokaryotic or eukaryotic host cells. For example, when a prokaryotic cell is used as the host cell, the expression vector used generally includes a strong promoter capable of initiating transcription (for example, $p_L^\lambda$ promoter, trp promoter, lac promoter, tac promoter, T7 promoter), a ribosome binding site for initiating translation, and a transcription/translation termination sequence. When a eukaryotic cell is used as the host cell, the vector may include an origin of replication acting in the eukaryotic cell, for example f1 origin of replication, SV40 origin of replication, pMB1 origin of replication, adeno origin of replication, AAV origin of replication, CMV origin of replication or BBV origin of replication, but is not limited thereto. A promoter in an expression vector for a eukaryotic host cell may be a promoter derived from a mammalian genome (for example, a metallothionein promoter) or a promoter derived from a mammalian virus (for example, an adenovirus late promoter, a vaccinia virus 7.5K promoter, a SV40 promoter, a cytomegalo virus (CMV) promoter, and a tk promoter of HSV). A transcription termination sequence in an expression vector for a eukaryotic host cell may be, in general, a polyadenylation sequence.

A vector system capable of expressing the heavy and light chain variable regions of the antibody may be a vector system in which the heavy and light chain variable regions are simultaneously expressed from a single vector, or a system in which the heavy and light chain variable regions are each independently expressed from separate vectors. In the latter case, the two vectors may be introduced into the host cell by co-transformation and targeted transformation.

According to an embodiment of the present invention, there is provided a host cell including a polynucleotide encoding a heavy chain variable region having an amino acid sequence of SEQ ID NO: 4 and a polynucleotide encoding a light chain variable region having an amino acid sequence of SEQ ID NO: 8.

According to an embodiment of the present invention, there is provided a host cell including a polynucleotide encoding a heavy chain variable region having an amino acid sequence of SEQ ID NO: 12 and a polynucleotide encoding a light chain variable region having an amino acid sequence of SEQ ID NO: 16.

The host cell may be transformed with a recombinant vector including a polynucleotide encoding a heavy chain variable region having an amino acid sequence of SEQ ID NO: 4 and a polynucleotide encoding a light chain variable region having an amino acid sequence of SEQ ID NO: 8. The host cell may also be transformed with a recombinant vector including a polynucleotide encoding a heavy chain variable region having an amino acid sequence of SEQ ID NO: 12 and a polynucleotide encoding a light chain variable region having an amino acid sequence of SEQ ID NO: 16.

The host cell, which is capable of stably and consecutively cloning or expressing the recombinant vector, may be any host cell known in the art. A prokaryotic host cell may be, for example, a *Bacillus* genus bacterium, such as *E. coli* JM109, *E. coli* BL21, *E. coli* RR1, *E. coli* LE392, *E. coli* B, *E. coli* X 1776, *E. coli* W3110, *Bacillus subtilis*, and *Bacillus thuringiensis*, or an intestinal bacterium, such as *Salmonella typhimurium*, *Serratia marcescens*, and various *Pseudomonas* species. A eukaryotic host cell may be, for example, a yeast (e.g., *Saccharomyce cerevisiae*), an insect cell, a plant cell, or an animal cell, for example, Sp2/0, CHO (Chinese hamster ovary) K1, CHO DG44, PER.C6, W138, BHK, COS-7, 293, HepG2, Huh7, 3T3, RIN, or a MDCK cell line.

The polynucleotide or the recombinant vector including the same may be transferred into the host cell using a method known in the art. For example, when a prokaryotic cell is used as a host cell, the transfer may be performed using a $CaCl_2$ method or an electroporation method, and when a eukaryotic cell is used as a host cell, the transfer may be performed by microinjection, calcium phosphate precipitation, electroporation, liposome-mediated transfection, or gene bombardment, but is not limited thereto.

When a microorganism, such as *E. coli*, is used as the host cell, the production is higher than that of an animal cell. However, it is not suitable for producing intact Ig-type antibodies due to incorrect glycosylation of the antibodies produced, although microorganisms may be used for producing antigen-binding fragments, such as Fab and Fv.

A transformed host cell may be selected using a phenotype expressed by a selectable marker by a method known in the art. For example, when the selectable marker is a specific antibiotic resistance gene, a transformant is cultured in a medium including the antibiotic, and thus a transformant may easily be selected.

According to an embodiment of the present invention, there is provided a hybridoma (Accession Number: KCLRF-BP-00221) cell that produces a monoclonal antibody specifically binding to angiopoietin-2.

According to an embodiment of the present invention, there is provided a hybridoma (Accession Number: KCLRF-BP-00222) cell that produces a monoclonal antibody specifically binding to angiopoietin-2.

An exemplary method of preparing a hybridoma cell will be described in detail below. The hybridoma cell lines prepared in the following Examples have been deposited in the Korean Cell Line Bank, Cancer Research Institute Seoul National University College of Medicine, 28 Yongon-dong, Chongno-Gu, Seoul, 110-744, Korea, which is an international depository authority under the Budapest Treaty, as of 6 Oct. 2009 and received Accession Nos: KCLRF-BP-00221 and KCLRF-BP-00222. The deposited hybridoma cell lines are kept according to the requirements of the Budapest Treaty for the deposition of a microorganism, and all restrictions imposed by the depositor on the availability to the public of the deposited material will be irrevocably removed upon the granting of the patent. Requests for such material may be subject to the requirements of 37 CFR 5 1.808 (b).

According to an embodiment of the present invention, there is provided a composition for preventing or treating an angiogenesis-related disease or cancer. The composition includes an antibody that specifically binds angiopoietin-2 disclosed herein, or an antigen binding fragment thereof; and a pharmaceutically acceptable excipient. The antibody or antigen binding fragment may be present in a therapeutically effective amount.

The composition may be used to prevent or treat cancer. Examples of the cancer include carcinoma, lymphoma, blastoma, sarcoma, and leukemia. In particular, the cancer may be squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, or various types of head and neck cancers, but are not limited thereto.

In addition, the composition may be used to prevent or treat an angiogenesis-related disease. Angiogenesis is a physiological process involving the formation of new capillary vessels from pre-existing vessels. If angiogenesis is not controlled autonomously, the vessels grow abnormally, causing diseases. Examples of an angiogenesis-related disease are rheumatoid arthritis, osteoarthritis, septic arthritis, psoriasis, corneal ulcer, age-related macular degeneration, diabetic retinopathy, proliferative vitreoretinopathy, premature retinopathy, keratoconus, Sjogren's syndrome, myopia ocular tumors, corneal graft rejection, abnormal wound healing, bone diseases, proteinuria, abdominal aortic aneurysm diseases, degenerative cartilage loss due to traumatic joint damage, nervous system demyelination diseases, liver cirrhosis, glomerular disease, premature rupture of embryonic membranes, inflammatory bowel disease, periodontal disease, arteriosclerosis, restenosis, central nervous system inflammation diseases, Alzheimer's disease, skin aging, and cancer invasion and metastasis, but are not limited thereto.

In an embodiment, the antibody or the antigen-binding fragment thereof may has a heavy chain variable region including at least one heavy chain CDR amino acid sequence selected from the group consisting of SEQ ID NO: 1, SEQ ID NO: 2, and SEQ ID NO: 3, and a light chain variable region including at least one light chain CDR amino acid sequence selected from the group consisting of SEQ ID NO: 5, SEQ ID NO: 6, and SEQ ID NO: 7, and specifically binds angiopoietin-2. In an embodiment, the antibody or antigen-binding fragment thereof has a heavy chain variable region including at least one heavy chain CDR amino acid sequence selected from the group consisting of SEQ ID NO: 9, SEQ ID NO: 10, and SEQ ID NO: 11, and a light chain variable region including at least one light chain CDR amino acid sequence selected from the group consisting of SEQ ID NO: 13, SEQ ID NO: 14, and SEQ ID NO: 15, and specifically binds angiopoietin-2.

In some embodiments, a monoclonal antibody that specifically binds angiopoietin-2 may be produced from a hybridoma cell having accession number KCLRF-BP-00221 or accession number KCLRF-BP-00222.

The composition for preventing or treating an angiogenesis-related disease or cancer includes a pharmaceutically acceptable excipient. The pharmaceutically acceptable excipient, which is commonly used in formulation, may be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The composition may further include a lubricant, a wetting agent, a sweetener, a flavor enhancer, an emulsifying agent, a suspension agent, or a preservative.

The composition for preventing or treating an angiogenesis-related disease or cancer may be administered orally or parenterally. Parenteral administration may include intravenous injection, subcutaneous injection, muscular injection, intraperitoneal injection, endothelial administration, local administration, intranasal administration, intrapulmonary administration, and rectal administration. Since oral administration leads to digestion of protein or peptide, the composition may be coated or otherwise formulated to prevent digestion of the antibody or antigen-binding fragment thereof. In addition, the composition may be administered by a device capable of targeting the active material to a target cell.

A suitable dose of the composition for preventing or treating an angiogenesis-related disease or cancer may depend on many factors, such as formulation methods, administration methods, ages of patients, body weight, gender, pathologic conditions, diets, administration time, administration route, excretion speed, and reaction sensitivity. A desirable dose of the composition may be in the range of about 0.001 to about 100 mg/kg for an adult. The term "therapeutically effective amount" used herein refers to a sufficient amount for preventing or treating cancer or an angiogenesis-related disease in a subject.

The composition may be formulated using a pharmaceutically acceptable excipient and/or an additive by a method known in the art. The composition may be prepared in a unit dose form or may be contained in a multi-dose container. The formulation may be a solution in oil or an aqueous medium, a suspension, a syrup, an emulsifying solution, an extract, powder, granules, a tablet, or a capsule, and may further include a dispersing or a stabilizing agent. In addition, the composition may be administered as an individual drug, or together with other drugs, and may be administered sequentially or simultaneously with other drugs.

The composition may be formulated as an immunoliposome, that is, a liposome that includes as a targeting ligand an antibody-derived protein. The liposome including the antibody may be prepared using a method known in the art. A liposome is a lipid composition including phosphatidylcholine, cholesterol, and polyethyleneglycol-derived phosphatidylethanolamine, and may be prepared, for example, by a reverse phase evaporation method. For example, F(ab')$_2$ fragments of an antibody may be adhered to the liposome through a thiol-disulfide exchange reaction. A chemical drug, such as doxorubicin, may be further included in liposome.

According to an embodiment of the present invention, there is provided a method of treating an angiogenesis-related disease or cancer of a subject, the method including administering to a subject a therapeutically effective amount of an antibody specifically binding to angiopoietin-2 or an antigen binding fragment thereof. The antibody or antigen binding fragment thereof may be in the form of a composition including a pharmaceutically acceptable excipient.

A detailed description of the composition for preventing or treating an angiogenesis-related disease or cancer and administration methods thereof are provided above.

The subjects to which the antibody is administered include animals. For example, the animals may be humans, dogs, cats, or mice.

A method of detecting angiopoietin-2 is also disclosed. The method includes contacting a sample isolated from a subject with an antibody specifically binding to angiopoietin-2. The method may provide information regarding angiopoietin-2 expression level in the sample needed for diagnosis, staging, or detection of cancer or an angiogenesis-related disease.

The sample isolated from a subject may be a sample isolated from a patient with the disease, e.g., cancer, or a normal person. In an embodiment, the sample may include tumor cells from a patient to assess the level of expression of angiopoietin-2 in order to permit staging of the patient's cancer. In an embodiment, the sample is a cell or tissue isolated from a human to detect the presence or absence of cancer in the sample or to determine whether there is a risk of the development of the cancer in the sample.

In some embodiments, the disease detected, staged or assessed for risk of development due to over-expression of angiopoietin-2 is a cancer or an angiogenesis-related disease disclosed above. The contacting may be performed by contacting the antibody specifically binding angiopoietin-2 with the sample such that if the antigen angiopoietin-2 exists in the sample the antibody will specifically bind the angiopoietin-2.

The antigen-antibody binding reaction may be detected using various immunoassay methods or immunostaining methods known in the art. Examples of immunoassay or immunostaining methods are radioimmunoassay, radioimmunoprecipitation, immunoprecipitation, ELISA, capture-ELISA, inhibition or competition assay, sandwich analysis, flow cytometry, immunofluorescence staining, and immunoaffinity purification, but are not limited thereto. For example, in an embodiment of a radioimmunoassay method, a radioisotope-labeled antibody may be used to detect angiopoietin-2. The radioisotope may be, for example, $C^{14}$, $I^{125}$, $P^{32}$, or $S^{35}$.

In an embodiment of an ELISA method, the method may include: (i) coating a surface of a solid substrate with a cell sample extract to be analyzed; (ii) incubating the cell sample extract with an antibody specifically binding to angiopoietin-2 as a first antibody; (iii) incubating the resultant product with a secondary antibody conjugated to an enzyme; and (iv) measuring the activity of the enzyme.

The solid substrate may be a hydrocarbon polymer such as polystyrene or polypropylene, glass, a metal, or a gel. For example, the solid substrate may be a microtiter plate. The enzyme conjugated to a secondary antibody may be an enzyme catalyzing a colorimetric, fluorometric, luminescence, or infra-red reactions, but is not limited thereto. For example, the enzyme may be alkaline phosphatase, β-galactosidase, horseradish peroxidase, luciferase, or Cytochrome $P_{450}$. When alkaline phosphatase is used, bromo-chloro-indolyl-phosphate (BCIP), nitro blue tetrazolium (NBT), naphthol-AS-B1-phosphate, or enhanced chemifluorescence (ECF) may be used as a substrate. When horseradish peroxidase is used, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), hypersensitive reaction solution (HYR: p-phenylenediamine-HCl and pyrocatechol), tetramethylbenzidine (TMB), 2,2'-Azine-di[3-ethylbenzthiazoline sulfonate] (ABTS), o-phenylenediamine (OPD) and naphtol/pyronin, glucose oxidase and t-nitroblue tetrazolium (t-NBT), or m-phenzaine methossulfate (m-PMS) may be used as a substrate.

The antibody specifically binding to angiopoietin-2 may have a label generating a detectable signal. The label may be a chemical label such as biotin; an enzymatic label such as alkaline phosphatase, β-galactosidase, horseradish peroxidase and Cytochrome $P_{450}$; a radioactive label such as $C^{14}$, $I^{125}$, $P^{32}$ and $S^{35}$; a fluorescent label such as fluorescein; a luminescent label; a chemiluminescent label; or a fluorescence resonance energy transfer (FRET) label, but is not limited thereto.

The final measurement of enzyme activities or signals in the ELISA method may be performed by any method known to one skilled in the art to enable quantitative or qualitative analysis of angiopoietin-2 amounts present in the sample. For example, signals could be detected easily by streptavidin in the case of a biotin-labeled antibody and by luciferin in the case of a luciferase-labeled antibody.

When an immunohistochemistry method is used, the method may include: (i) immobilizing a cell or tissue sample to be analyzed and sectioning thereof; (ii) incubating the section with an antibody specifically binding to angiopoietin-2 as a first antibody; (iii) reacting the resultant product with a secondary antibody conjugated to an enzyme; and (iv) measuring the activity of the enzyme.

Methods for immobilizing and sectioning the sample are well known in the art. For example, the sample may be immobilized using a chemical material such as formalin. In addition, the section may be produced after the sample is embedded in a material such as paraffin. When paraffin is used in the production of the section, paraffinization may be performed to easily react an antigen in the cell or tissue sample with the first antibody. The operations (iii) and (iv) have already been described above with respect to the ELISA method.

The disease may be diagnosed, staged, or detected by analyzing the intensity of the signals from the immunoassay indicating the presence of an antibody-angiopoietin-2 complex. In other words, when, for example, the signal indicating the presence of an antibody-angiopoietin-2 complex from a test sample is stronger than the corresponding signal from a normal control sample, the test sample may be determined to have higher expression of angiopoietin-2 and therefore determined to have an angiogenesis-related disease present. Therefore the subject from whom the test sample was obtained may be diagnosed as having an angiogenesis-related disease.

One or more embodiments of the present invention will now be described in further detail with reference to the following Examples. However, these examples are for the illustrative purposes only and are not intended to limit the scope of the invention.

Example 1

Preparation of Hybridomas that Produce a Monoclonal Antibody Specifically Binding to Angiopoietin-2 and Production of Monoclonal Antibodies SAIT-Ang-2-5 and SAIT-Ang-2-6

The process of producing hybridoma cell clones and obtaining monoclonal antibodies, described below, is schematically illustrated in FIG. 1.

(1) Immunization of Mice

To obtain immunized mice necessary for developing hybridoma cell lines, 500 μg angiopoietin-2 secreted from a human umbilical vein endothelial cell (HUVEC) emulsified in an equal volume of complete Freund's adjuvant was administered via intraperitoneal injection to each of five female 5-week-old BALB/c mice (Japan SLC, Inc.). After two weeks, 250 μg antigen mixed with incomplete Freund's adjuvant was administered to each mouse via intraperitoneal injection. After one additional week, a final boosting with the antigen in incomplete Freund's adjuvant was performed. Blood was collected from the tail of each mouse three days after the final boosting to obtain serum, which was diluted at $1/1000$ with phosphate buffered saline (PBS) and subjected to an enzyme-linked immunosorbent assay (ELISA) to determine the titer of an antibody recognizing angiopoietin-2. From the results, mice in which a sufficient amount of the antibody was obtained were selected for performing cell fusion.

(2) Cell Fusion and Preparation of Hybridoma Cells

Three days before a cell fusion experiment, 50 μg angiopoietin-2 in PBS was administered via intraperitoneal injection to the mice. Each immunized mouse was anesthetized, and the spleen was taken out. The extracted spleen was ground with a mesh to isolate cells, which were mixed with Dulbecco's Modified Eagle medium (DMEM) to prepare a spleen cell suspension. The suspension was centrifuged to collect the cell layer. Then, spleen cells were mixed with mouse myeloma cells (Sp2/0) and centrifuged to precipitate the cells. The precipitate was slowly dispersed, treated with 1 ml 45% polyethylene glycol (PEG) in DMEM, and maintained at 37° C. for one minute before adding 1 ml DMEM. Subsequently, 10 ml DMEM was added to the resultant for 1 minute, and incubated in a water bath at 37° C. for 5 minutes. The cell suspension was re-centrifuged after the total volume was made to reach 50 ml. The resulting cell precipitate was re-suspended in an isolation medium, hypoxanthine aminopterin thymidine (HAT) medium at a concentration of $1-2\times10^5$ cells/ml. Then, 0.1 ml aliquots of the cell suspension were distributed into wells of a 96-well plate and incubated in a carbon dioxide incubator at 37° C. to prepare hybridoma cells.

(3) Selection of Hybridoma Cells that Produce Monoclonal Antibody with Respect to Angiopoietin-2

The hybridoma cells prepared above in (2) were screened by ELISA analysis to select hybridoma cells specifically binding to angiopoietin-2.

50 μl (2 μg/ml) angiopoietin-2 was added to each well of a microtiter plate to attach to the surface of the microtiter plate. Unreacted antigen was removed by washing. 50 μl of a hybridoma cell culture was added to each well of the microtiter plate to react with the attached antigens for 1 hour. Then, the wells were washed with a phosphate-buffered saline-TWEEN 20 (PBST) solution to remove unbound cells. Goat anti-mouse IgG-horseradish peroxidase (IgG-HRP) was added to the wells, incubated at room temperature for 1 hour and then the wells were washed with phosphate buffered saline TWEEN-20 (PBST) solution. Subsequently, a solution of o-phenylenediamine dihydrochloride (OPD), a substrate for colorimetric detection of HRP activity in ELISA, was added to the wells, and the degree of reaction was evaluated by measuring absorption at 450 nm using an ELISA reader. In such a manner, hybridoma cell lines producing an antibody highly specific for angiopoietin-2 were repeatedly selected. A limiting dilution was performed on the selected hybridoma cell lines to obtain two clones of hybridoma cell lines, each producing a monoclonal antibody. The two monoclonal antibodies were named SAIT-Ang-2-5 and SAIT-Ang-2-6, respectively. The two final hybridoma cell lines producing SAIT-Ang-2-5 and SAIT-Ang-2-6, respectively, were deposited in the Korean Cell Line Bank and received accession number KCLRF-BP-00221 and accession number KCLRF-BP-00222, respectively.

(4) Production and Purification of Monoclonal Antibody

The hybridoma cells obtained in (3) above were cultured in a serum free medium to produce monoclonal antibodies for purification from the culture.

SAIT-Ang-2-5-producing-hybridoma cells cultured in 50 ml DMEM including 10% fetal bovine serum (FBS) were centrifuged to obtain a cell precipitate. The cell precipitate was washed with 20 ml PBS at least twice to remove the FBS. The cell precipitate was re-suspended in 50 ml DMEM and then incubated in a carbon dioxide incubator at 37° C. for 3 days. Subsequently, the cell culture was centrifuged to remove the antibody-producing cells. The culture medium including antibodies was isolated and either stored at 4° C. or used directly. Antibodies were further purified from 50 to 300 ml of the culture medium using an AKTA purification device (GE Health) equipped with an affinity column (protein G agarose column; Pharmacia, USA). The purified antibodies were stored for subsequent use after replacing the supernatant with PBS using a filter for protein aggregation (Amicon).

The monoclonal antibody SAIT-Ang 2-6 was produced from SAIT-Ang 2-6-producing hybridoma cells and purified using the same procedures.

Example 2

Determination of Whether Binding Between Angiopoietin-2 and Tie-2 is Neutralized by Competitive ELISA A 96-well MaxiSorp™ flat-bottom plate (Nunc) was coated with recombinant human Tie2-Fc (hTie2-Fc) (R&D Systems, Inc.) dissolved in DMEM culture containing 50 μg/ml bovine serum albumin (BSA). The hTie-2Fc is a chimeric protein including the water-soluble extracellular region of human Tie-2 and the Fc fragment of human $IgG_1$. The concentration of hTie2-Fc immobilized was equivalent to 75% of its maximum binding concentration with 1 nM of recombinant hAng-2 (a recombinant human angiopoietin-2 protein with an attached His tag; R&D Systems). The plate was washed with Phosphate Buffered Saline (PBS) containing 0.1% TWEEN-20 five times and blocked with PBS containing 5% BSA at room temperature for two hours. To perform an ELISA experiment for determining whether binding between angiopoietin-2 and Tie-2 was neutralized, each of the monoclonal antibodies SAIT-Ang-2-5 and SAIT-Ang-2-6 prepared according to Example 1 were serially diluted from 100 nM by one-fourth each time with PBS containing 1% BSA and 1 nM hAng-2 and adjusted to a concentration of 6.1 pM. Then, 100 μl of the antibody/hAng-2 solution was added to each well and left to react at room temperature for two hours. Then, the wells were washed with PBS containing 0.1% Tween-20 five times, and anti-His antibodies (GE Healthcare) were diluted to about 1:3,000 with PBS containing 1% BSA, added to the wells, and left to react at room temperature for one hour. Subsequently, 100 µl of goat anti-mouse-IgG-HRP (Pierce) diluted with PBS containing 1% BSA to about 1:10,000 was added to each well of the plate, left to react at room temperature for one hour, and washed with PBS containing 0.1% Tween-20 five times. Lastly, 100 µl trimethylbenzidine (TMB) (SIGMA), a horseradish peroxidase substrate, was added to each well of the plate to induce a color reaction. The reaction was stopped by adding 50 µl of 5 N $H_2SO_4$ solution. The $OD_{450}$ value was read on a plate reader (Molecular Devices). From the values, the 50% inhibition concentration ($IC_{50}$) for the angiopoietin-2:Tie-2 binding capacity was determined. Based on the results, each of the monoclonal antibodies SAIT-Ang-2-5 and SAIT-Ang-2-6 of Example 1 was determined to be capable of neutralizing binding between angiopoietin-2 and Tie-2 (refer to Table 1).

TABLE 1

| Antibody name | 50% inhibition concentration for the binding between angiopoietin-2 and Tie-2 ($IC_{50}$, nM) |
| --- | --- |
| Control | >100 |
| Monoclonal antibody SAITAng-2-5 | 0.764 |
| Monoclonal antibody SAITAng-2-6 | 1.859 |

Example 3

Affinity Measurement of Monoclonal Antibodies SAIT-Ang-2-5 and SAIT-Ang-2-6

The affinity of each of the monoclonal antibodies SAIT-Ang-2-5 and SAIT-Ang-2-6 of Example 1 to angiopoietin-2 was measured using a surface plasmon resonance (SPR) device (BIAcore T100, GE Healthcare). 20 µg/ml recombinant hAng-2 (R&D Systems) was immobilized on a CM5 chip (GE Healthcare) using a pH 4.5 acetate solution and an amine coupling kit (GE Healthcare). Each of the monoclonal antibodies SAIT-Ang-2-5 and SAIT-Ang-2-6 of Example 1 was diluted to eight different concentrations down to 0.78125 nM by serially diluting to ½ each time starting from 100 nM. Then, the antigen/antibody affinity was measured by binding each antibody with the antigen immobilized on the CM5 chip and dissociating the antigen from the antibody using a pH2.2 glycine-HCl solution. As shown in Table 2 below, values of $K_a$(on) and $K_b$(off) were obtained, and $K_d$ values were calculated therefrom. From the results, the affinity of each monoclonal antibody SAIT-Ang-2-5 and SAIT-Ang-2-6 of Example 1 to angiopoietin-2 was determined.

TABLE 2

| Name | On rate (1/Ms) | Off rate (1/s) | Affinity (Kd, nM) |
| --- | --- | --- | --- |
| Monoclonal antibody SAIT-Ang-2-5 | $1.972 \times 10^6$ | $1.778 \times 10^{-3}$ | 0.902 |
| Monoclonal antibody SAIT-Ang-2-6 | $1.635 \times 10^6$ | $2.072 \times 10^{-3}$ | 1.267 |

Example 4

Monoclonal Antibodies SAIT-Ang-2-5 and SAIT-Ang-2-6 Inhibit Angiogenesis

To determine angiogenesis inhibition effects of the monoclonal antibodies SAIT-Ang-2-5 and SAIT-Ang-2-6 of Example 1, an endothelial cell angiogenesis assay was performed using BD BioCoat™ Angiogenesis System-Endothelial Cell Tube Formation (BD Biosciences).

A BD Falcon 96-well Black/Clear plate coated with BD MATRIGEL™ Matrix that had been stored at −20° C. was slowly thawed at 4° C. for 6 hours, and the mat cover of the plate was removed inside a sterile clean bench. Then, the plate was left at 37° C. under 5% $CO_2$ condition for 30 minutes to allow the MATRIGEL™ Matrix to form polymers.

Human umbilical vein endothelial cells (HUVEC) were cultured to 70 to 80% confluence on a petridish containing endothelial basal medium (EBM) (Lonza) with 2% fetal bovine serum and 0.5% Trypsin-EDTA (Gibco). Then, the cells were re-suspended in a culture containing 2% fetal bovine serum and 100 ng/ml of angiopoietin-2 to a cell concentration of $4 \times 10^5$ cells/ml. At this time, 0.05 µM, 0.1 µM, or 0.2 µM of monoclonal antibodies SAIT-Ang-2-5 or SAIT-Ang-2-6 of Example 1 was added to the cell suspension.

Then, 50 µl (about $2 \times 10^4$ cells) of the cell suspension was added to each well of the plate and incubated at 37° C. under 5% $CO_2$ condition for 18 hours. Then, the culture medium was removed and each well was washed twice with 100 µl of Hanks' balanced salt solution (HBSS, Invitrogen) ensuring that the tubes of the cells formed on BD Matrigel™ Matrix were not damaged. 50 µl of calcein AM (BD BIOsciences) dissolved in HBSS at 8 µg/ml was added to each well. The plate was then left to react at 37° C. under 5% $CO_2$ condition for 30 minutes. The calcein AM (BD sciences) solution was removed and the plate was washed with HBSS twice. An image of the plate was obtained on a fluorescent microscope (see FIG. 2A) and analyzed to determine tube length formed using METAMORPH® software (Universal Imaging Corporation™, Molecular Devices, Inc.). Tube length results as a function of concentration of SAIT-Ang-2-5 or SAIT-Ang-2-6 added to the cell culture are presented in the histographs of FIG. 2B.

Figure 2A:
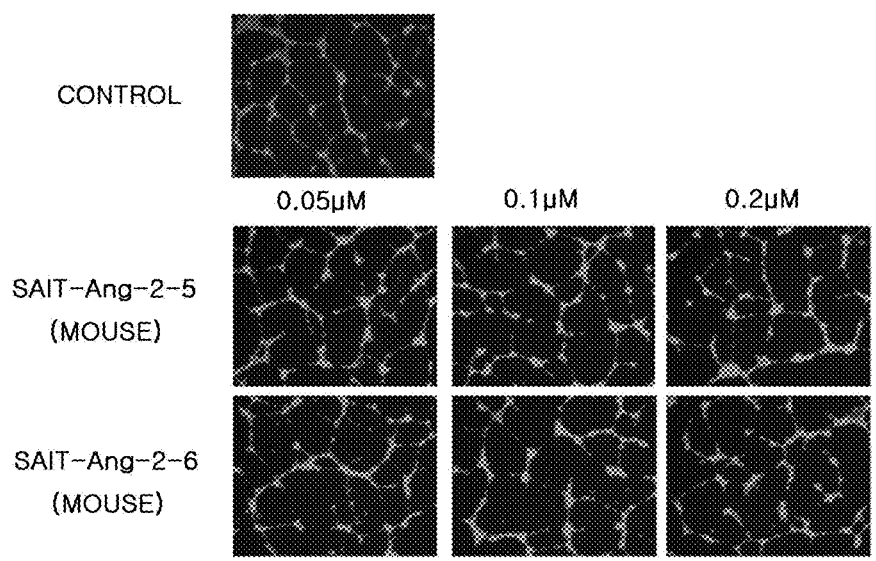
FIGS. 2A and 2B are, respectively, fluorescent microscope images and histograms showing results of assays of angiogenesis of endothelial cells as a function of concentration of monoclonal antibody SAIT-Ang-2-5 or SAIT-Ang-2-6, according to embodiments of the present invention.
Figure 2B:
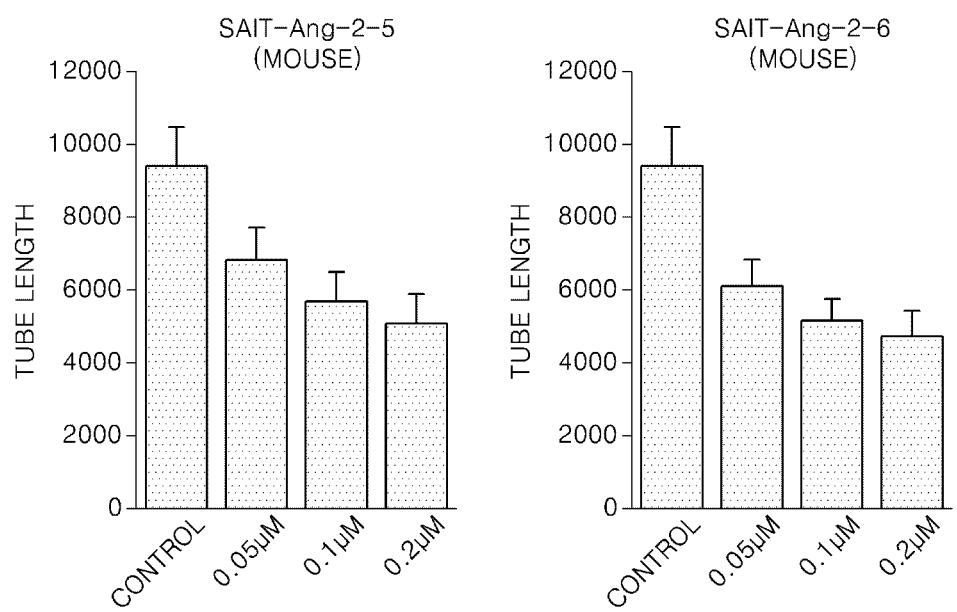

As illustrated in FIGS. 2A and 2B, the monoclonal antibodies SAIT-Ang-2-5 and SAIT-Ang-2-6 inhibited angiogenesis of HUVEC.

Example 5

Monoclonal Antibodies SAIT-Ang-2-5 and SAIT-Ang-2-6 Inhibit Proliferation of Tumor Cells Experiments were performed to determine the effects of each of the monoclonal antibodies SAIT-Ang-2-5 and SAIT-Ang-2-6 of Example 1 on proliferation of tumor cells in a mouse xenograft model transplanted with human colorectal cancer cell line HT-29.

Figure 3A:
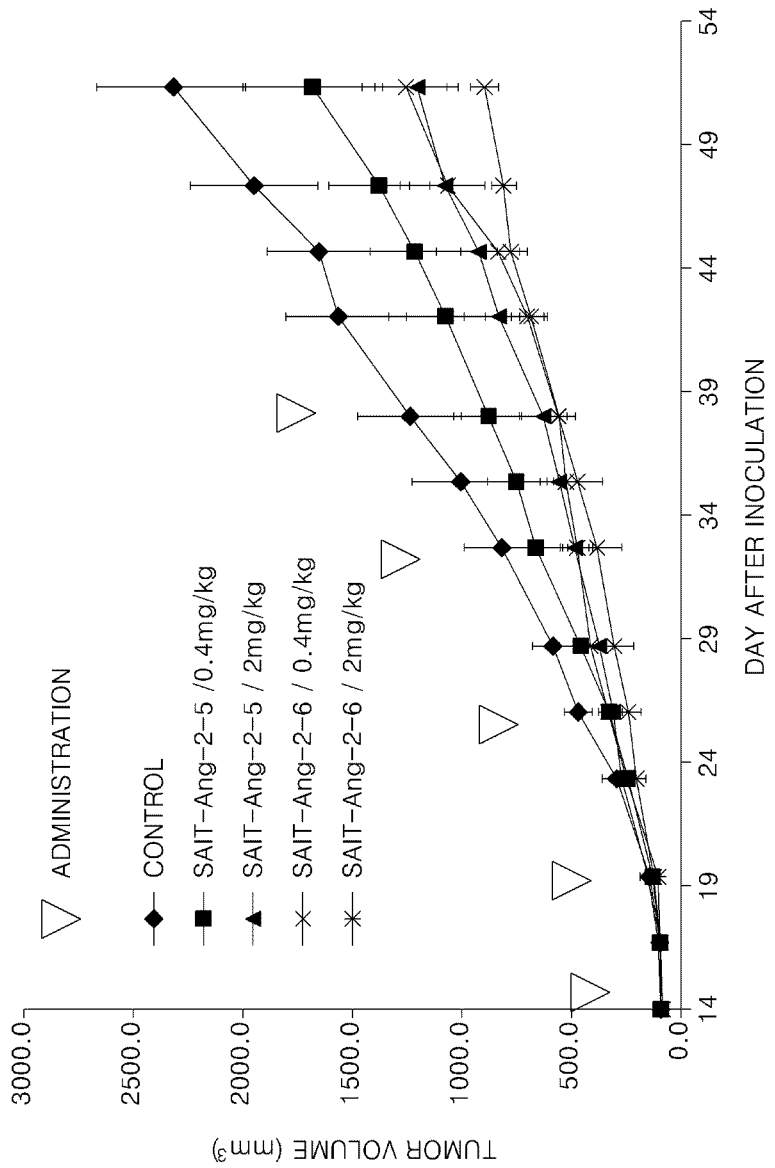
FIG. 3A is a graph of tumor volume as a function of time for five treatment groups, according to embodiments of the present invention.
Figure 3B:
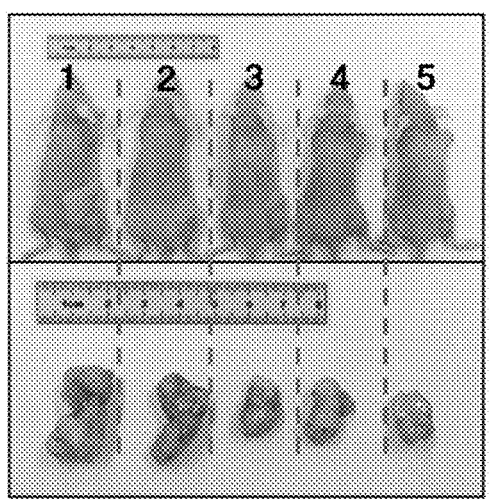
FIG. 3B is an image of representative mice and their tumors with a tabulation of the average tumor mass for each of five treatment groups, according to embodiments of the present invention.

The mouse model used was obtained by administering 50 µl of human colorectal cancer cell line HT-29 ($5 \times 10^6$ cells) via subcutaneous injection to female 6-week-old BALB/c nude mice and selecting 6 mice with a tumor size in the range of about 50 to about 150 mm³ for each of the five treatment groups (control, 0.4 mg/kg SAIT-Ang-2-5, 2 mg/kg SAIT-Ang-2-5, 0.4 mg/kg SAIT-Ang-2-6, and 2 mg/kg SAIT-Ang-2-6). The appropriate concentration of SAIT-Ang-2-5 or SAIT-Ang-2-6 was administered via intraperitoneal injection to the mice in its treatment group five times 2-3 weeks after tumor cells were formed. FIG. 3A presents a graph of tumor volume as a function of time after inoculation with the tumor cells for each of the five treatment groups. The administration time points for the five intraperitoneal injections are shown on the graph. FIG. 3B presents images of representative mice and tumors, as well as average tumor mass, for each of the five treatment groups.

Referring to FIGS. 3A and 3B, when 2 mg/kg of either monoclonal antibody is administered, the size and weight of the tumor are much smaller than those of the control.

Example 6

Cloning the Mouse Anti-Angiopoietin-2 Antibody Gene for Preparation of a Humanized Chimeric Antibody To prepare a humanized chimeric antibody including the heavy and light chain variable regions of the monoclonal antibody SAIT-Ang-2-5 or SAIT-Ang-2-6, total RNA was first obtained from hybridoma cells ($2\times10^6$ cells) producing monoclonal antibody SAIT-Ang-2-5 or SAIT-Ang-2-6, respectively, using a RIBOPURE™ Kit (Ambion). The RNA was used as the template to synthesize single-stranded cDNA using a PROTOSCRIPT®First Strand cDNA Synthesis Kit (New England Biolab). Subsequently, only the gene sequences of the heavy and light chain variable regions of each monoclonal antibody were amplified by using a mouse Ig-primer set (Novagen). The amplification process was performed using a GeneAmp PCR System 9700 (Applied Biosystem) with the following PCR conditions: at 94° C. for 5 minutes; 35 cycles at 94° C. for 1 minute, 60° C. for 1 minute, and 72° C. for 2 minutes; at 72° C. for 6 minutes; cooling down to 4° C. The amplified PCR products were washed using a QIAquick Multiwell PCR Purification kit (Qiagen) according to the manufacture's protocol.

The PCR products were cloned into pGEM-T Easy vector (Promega), and sequenced (SolGent Co., Ltd, Daejeon city, Korea). As a result, the CDR sequences as shown in Table 3 below were obtained.

Example 7

Expression and Purification of Humanized Chimeric Antibody

For either antibody, the heavy and light chain variable regions obtained according to Example 6 were respectively cloned into different vectors. The heavy chain variable region was cloned into a vector including a CMV promoter and the constant region and the Fc region of human IgG1. The light chain variable region was cloned into a vector including a CMV promoter and the constant region of human IgG1. In particular, the heavy chain variable region and the vector to receive the heavy chain variable region were digested with restriction enzymes SfiI (Roche) and NheI (Roche) and the light chain variable region and the vector to receive the light chain variable region were digested with restriction enzymes SfiI (Roche) and BglII (Roche). Each region was ligated into the corresponding vector by T4 DNA ligase (New England Biolab) to prepare a heavy chain vector and a light chain vector for expressing each humanized chimeric antibody. The heavy and light chain vectors were simultaneously transfected into HEK-293E cell distributed by Korea Research Institute of Biotechnology. The HEK-293E cells were cultured in a serum-free DMEM (Invitrogen), which was changed four times at three day intervals. The culture medium containing the expressed humanized chimeric antibody was centrifuged to remove residues and impurities. Then, each monoclonal antibody was purified by affinity chromatography using protein A having strong affinity with the Fc region of the antibody by using a method known in the art.

Example 8

Humanized Chimeric Antibody Having Effects of Inhibiting Angiogenesis

An endothelial cell angiogenesis assay was performed with each of the two humanized chimeric antibodies prepared according to Example 7 using the BD BioCoat™ Angiogenesis System-Endothelial Cell Tube Formation (BD Biosciences) assay described in Example 4 was used to determine whether the two humanized chimeric antibodies inhibit angiogenesis. Results from the assays are shown in FIGS. 4A and 4B.

Figure 4A:
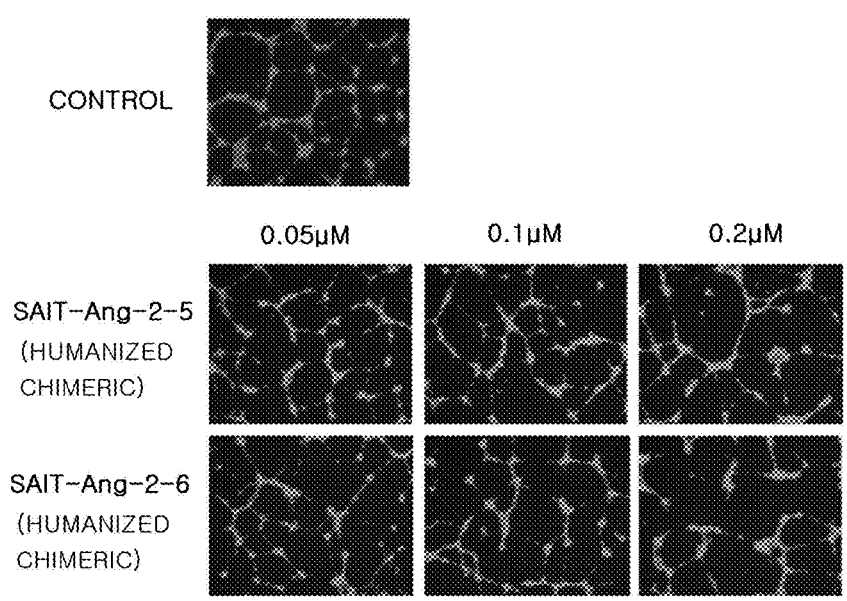
FIGS. 4A and 4B are, respectively, fluorescent microscope images and histograms showing results of assays of angiogenesis of endothelial cells as a function of concentration of a humanized chimeric antibody including the heavy and light chain variable regions of monoclonal antibody SAIT-Ang-2-5 or monoclonal antibody SAIT-Ang-2-6, according to embodiments of the present invention.
Figure 4B:
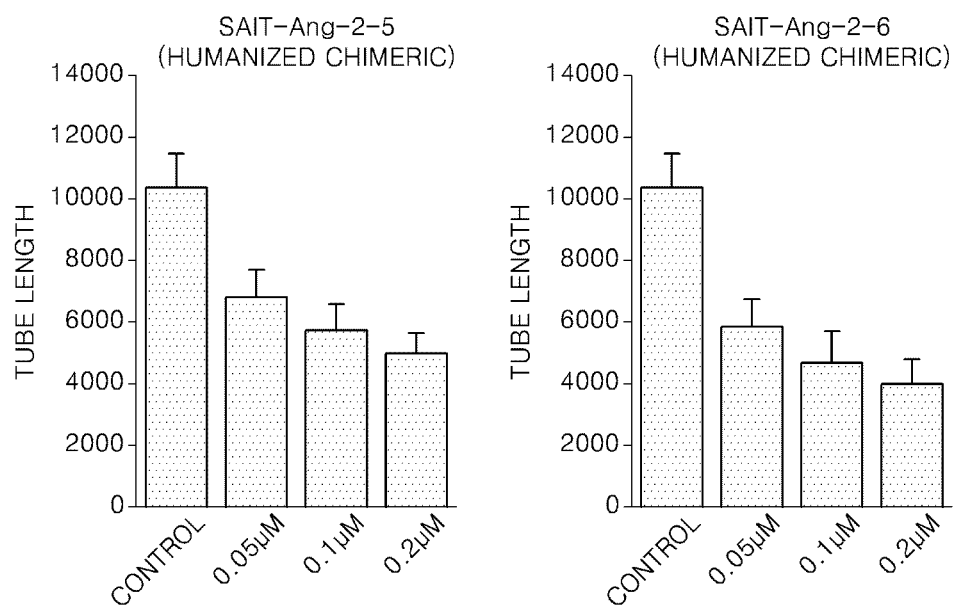

As illustrated in FIGS. 4A and 4B, the humanized chimeric antibody including the heavy and light chain variable regions of monoclonal antibody SAIT-Ang-2-5 and the humanized chimeric antibody including the heavy and light chain variable regions of monoclonal antibody SAIT-Ang-2-6 inhibited angiogenesis of HUVEC, as did monoclonal antibodies SAIT-Ang-2-5 and SAIT-Ang-2-6.

Example 9

CDR Amino Acid Sequences of Monoclonal Antibodies SAIT-Ang-2-5 and SAIT-Ang-2-6

The heavy and light chain CDR amino acid sequences of monoclonal antibodies SAIT-Ang-2-5 and SAIT-Ang-2-6 of Example 1, which play a key role in antigen recognition, are shown in Table 3 below. The sequences shown in Table 3 were confirmed to be different from CDR amino acid sequences of other antibodies known to recognize angiopoietin-2.

TABLE 3

| | CDR1 amino acid sequence | CDR2 amino acid sequence | CDR3 amino acid sequence |
|---|---|---|---|
| SAIT-Ang-2-5 heavy chain | NFGMH (SEQ ID NO: 1) | YISSGSDTIYY ADTVKG (SEQ ID NO: 2) | ESTMITMGYVLD YWGQGTSV (SEQ ID NO: 3) |
| SAIT-Ang-2-5 light chain | LASQTIGTWLA (SEQ ID NO: 5) | AATSLAD (SEQ ID NO: 6) | QQLYSIPLTIGA (SEQ ID NO: 7) |
| SAIT-Ang-2-6 heavy chain | NYLMH (SEQ ID NO: 9) | NIYPGSGATNY DEKFKS (SEQ ID NO: 10) | DDYDGSWFAYWG QGTLV (SEQ ID NO: 11) |
| SAIT-Ang-2-6 light chain | KSSQSLLISGN QKNFLA (SEQ ID NO: 13) | GASTRDS (SEQ ID NO: 14) | QNDHSYPLTFGT (SEQ ID NO: 15) |

As described above, an antibody specifically binding to angiopoietin-2, or antigen-binding fragments thereof, and a composition including the antibody or an antigen-binding fragment thereof, may efficiently prevent or treat angiogenesis-related disease or cancer.

The terminology used herein is for the purpose of describing particular embodiments only and is not intended to be limiting of the invention. As used herein, the singular forms "a," "an" and "the" are intended to include the plural forms as well, unless the context clearly indicates otherwise. The terms "comprising", "having", "including", and "containing" are to be construed as open-ended terms (i.e. meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. No language in the specification should be construed as indicating any non-claimed element as essential to the practice of the invention as used herein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A hybridoma cell having Accession Number KCLRF-BP-00221 or Accession Number KCLRF-BP-00222.

2. An isolated monoclonal antibody produced from the hybridoma cell of claim 1, wherein the monoclonal antibody specifically binds to angiopoietin-2.

3. The monoclonal antibody of claim 2, comprising an IgG1-type antibody.

4. The monoclonal antibody of claim 2, wherein the angiopoietin-2 is from a human or mouse.

5. An isolated antigen binding fragment of the monoclonal antibody of claim 2.

6. A composition comprising the antibody of claim 2, or an antigen binding fragment thereof, and a pharmaceutically acceptable excipient.

7. An isolated antibody specifically binding to angiopoietin-2, the antibody comprising
a heavy chain variable region comprising complementarity determining region (CDR) amino acid sequences SEQ ID NO: 1, SEQ ID NO: 2, and SEQ ID NO: 3, and
a light chain variable region comprising CDR amino acid sequences SEQ ID NO: 5, SEQ ID NO: 6, and SEQ ID NO: 7.

8. The antibody of claim 7, wherein the heavy chain variable region comprises an amino acid sequence of SEQ ID NO: 4, and the light chain variable region comprises an amino acid sequence of SEQ ID NO: 8.

9. The antibody of claim 7, wherein the antibody is an antigen-binding antibody fragment.

10. A composition comprising the antibody of claim 7, or an antigen binding fragment thereof, and a pharmaceutically acceptable excipient.

11. An isolated antibody specifically binding to angiopoietin-2, or an antigen binding fragment thereof, the antibody comprising
a heavy chain variable region comprising CDR amino acid sequences SEQ ID NO: 9, SEQ ID NO: 10, and SEQ ID NO: 11, and
a light chain variable region comprising CDR amino acid sequences SEQ ID NO: 13, SEQ ID NO: 14, and SEQ ID NO: 15.

12. The antibody of claim 11, wherein the heavy chain variable region comprises an amino acid sequence of SEQ ID NO: 12, and the light chain variable region comprises an amino acid sequence of SEQ ID NO: 16.

13. The antibody of claim 11, wherein the antibody is an antigen-binding antibody fragment.

14. A composition comprising the antibody of claim 11, or an antigen binding fragment thereof, and a pharmaceutically acceptable excipient.

* * * * *